US008592483B2

(12) United States Patent
Ueno

(10) Patent No.: US 8,592,483 B2
(45) Date of Patent: Nov. 26, 2013

(54) METHOD FOR TREATING SCHIZOPHRENIA

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 13/566,353

(22) Filed: Aug. 3, 2012

(65) Prior Publication Data

US 2013/0035393 A1 Feb. 7, 2013

Related U.S. Application Data

(60) Provisional application No. 61/515,418, filed on Aug. 5, 2011.

(51) Int. Cl.
*A01N 37/08* (2006.01)
*A61K 31/557* (2006.01)
*C07C 59/185* (2006.01)

(52) U.S. Cl.
USPC .......................... 514/573; 554/117; 554/118

(58) Field of Classification Search
USPC ....................................................... 514/573
See application file for complete search history.

(56) References Cited

U.S. PATENT DOCUMENTS

| | | |
|---|---|---|
| 5,073,569 A | 12/1991 | Ueno et al. |
| 5,106,869 A | 4/1992 | Ueno et al. |
| 5,117,042 A | 5/1992 | Ueno et al. |
| 5,166,174 A | 11/1992 | Ueno et al. |
| 5,212,324 A | 5/1993 | Ueno |
| 5,221,763 A | 6/1993 | Ueno et al. |
| 5,225,439 A | 7/1993 | Ueno et al. |
| 5,290,811 A | 3/1994 | Ueno et al. |
| 5,380,709 A | 1/1995 | Ueno et al. |
| 5,426,115 A | 6/1995 | Ueno et al. |
| 5,428,062 A | 6/1995 | Ueno et al. |
| 5,534,547 A | 7/1996 | Ueno et al. |
| 5,591,887 A | 1/1997 | Ueno et al. |
| 5,739,161 A | 4/1998 | Ueno |
| 5,770,759 A | 6/1998 | Ueno et al. |
| 5,886,034 A | 3/1999 | Ueno et al. |
| 6,242,485 B1 | 6/2001 | Ueno |
| 6,265,440 B1 | 7/2001 | Ueno et al. |
| 7,098,233 B2 * | 8/2006 | Di Cesare et al. ............ 514/415 |
| 7,232,929 B2 * | 6/2007 | Bialer et al. .................... 564/86 |
| 8,202,909 B2 * | 6/2012 | Ueno ............................. 514/573 |
| 2006/0194880 A1 * | 8/2006 | Ueno ............................. 514/573 |
| 2008/0255203 A1 * | 10/2008 | Lee et al. ...................... 514/340 |
| 2012/0225938 A1 | 9/2012 | Ueno |

FOREIGN PATENT DOCUMENTS

WO WO 2012100347 A1 * 8/2012

OTHER PUBLICATIONS

Horrobin, D.F. Schizophrenia as a Prostaglandin Deficiency Disease, Apr. 30, 1977, The Lancet, vol. 1, Issue 8018, pp. 936-937.*
Schizophrenia, NIH Publication No. 9-3517, revised 2009, U.S. Department of Health and Human Services, National Institute of Mental Health.
International Search Report and Written Opinion for Application No. PCT/JP2012/070411 mail date Oct. 16, 2012.
T. Michio; Brain and arachidonic acid cascade, Endogenous psychosis and prostaglandin, Gendai iryo, 1988, vol. 20, No. 11, p. 3140-3143.
J. Cuppoletti et al; Cellular and molecular effects of unoprostone as BK channel activator, Biochim Biophys Acta, 2007, vol. 1768, No. 5, p. 1083-92.
A. K. Bassil et al; Activation of prostaglandin EP receptors by lubiprostone in rat and human stomach and colon, Br J Pharmacol, 2008, vol. 154, No. 1, p. 126-35.

* cited by examiner

*Primary Examiner* — Jeffrey S. Lundgren
*Assistant Examiner* — Tori M Strong
(74) *Attorney, Agent, or Firm* — Sughrue Mion, PLLC

(57) ABSTRACT

The present invention provides a novel fatty acid derivative. The present invention also provides a method for treating schizophrenia in a mammalian subject, which comprises administering to the subject in need thereof an effective amount of a fatty acid derivative.

4 Claims, No Drawings

METHOD FOR TREATING SCHIZOPHRENIA

TECHNICAL FIELD

The present invention relates to a method for treating schizophrenia.

BACKGROUND

Schizophrenia is a chronic, severe, and disabling brain disorder that has affected people throughout history. About 1 percent of Americans have this illness.

People with the disorder may hear voices other people don't hear. They may believe other people are reading their minds, controlling their thoughts, or plotting to harm them. This can terrify people with the illness and make them withdrawn or extremely agitated.

People with schizophrenia may not make sense when they talk. They may sit for hours without moving or talking. Sometimes people with schizophrenia seem perfectly fine until they talk about what they are really thinking.

Families and society are affected by schizophrenia too. Many people with schizophrenia have difficulty holding a job or caring for themselves, so they rely on others for help.

Treatment helps relieve many symptoms of schizophrenia, but most people who have the disorder cope with symptoms throughout their lives. However, many people with schizophrenia can lead rewarding and meaningful lives in their communities. Researchers are developing more effective medications and using new research tools to understand the causes of schizophrenia. In the years to come, this work may help prevent and better treat the illness.

The symptoms of schizophrenia fall into three broad categories: positive symptoms, negative symptoms, and cognitive symptoms. Positive symptoms are psychotic behaviors not seen in healthy people. People with positive symptoms often "lose touch" with reality. These symptoms can come and go. Sometimes they are severe and at other times hardly noticeable, depending on whether the individual is receiving treatment. They include hallucinations, delusions, thought disorders and movement disorders. Negative symptoms are associated with disruptions to normal emotions and behaviors. These symptoms are harder to recognize as part of the disorder and can be mistaken for depression or other conditions. These symptoms include "flat affect" (a person's face does not move or he or she talks in a dull ore monotonous voice), lack of pleasure in everyday life, lack of ability to begin and sustain planned activities, and speaking little, even when forced to interact. Cognitive symptoms are subtle. Like negative symptoms, cognitive symptoms may be difficult to recognize as part of the disorder. Often, they are detected only when other tests are performed. Cognitive symptoms include poor "executive functioning" (the ability to understand information and use it to make decisions), trouble focusing or paying attention and problems with "working memory" (the ability to use information immediately after learning it).

Because the causes of schizophrenia are still unknown, treatments focus on eliminating the symptoms of the disease. Treatments include antipsychotic medications and various psychosocial treatments (Schizophrenia, NIH Publication No. 09-3517, revised 2009, National Institute of Mental Health), but satisfied treatment has not been established.

Fatty acid derivatives are members of class of organic carboxylic acids, which are contained in tissues or organs of human or other mammals, and exhibit a wide range of physiological activity. Some fatty acid derivatives found in nature generally have a prostanoic acid skeleton as shown in the formula (A):

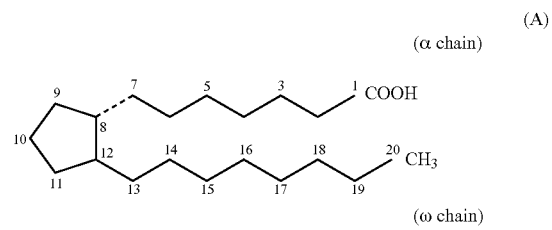

On the other hand, some of synthetic prostaglandin (PG) analogues have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a (β-configuration).

PGs are known to have various pharmacological and physiological activities, for example, vasodilatation, inducing of inflammation, platelet aggregation, stimulating uterine muscle, stimulating intestinal muscle, anti-ulcer effect and the like.

Prostones, having an oxo group at position 15 of prostanoic acid skeleton (15-keto type) and having a single bond between positions 13 and 14 and an oxo group at position 15 (13,14-dihydro-15-keto type), are fatty acid derivatives known as substances naturally produced by enzymatic actions during metabolism of the primary PGs and have some therapeutic effect. Prostones have been disclosed in U.S. Pat. Nos. 5,073,569, 5,534,547, 5,225,439, 5,166,174, 5,428,062 5,380,709 5,886,034 6,265,440, 5,106,869, 5,221,763, 5,591, 887, 5,770,759 and 5,739,161, the contents of these references are herein incorporated by reference.

However it is not known how fatty acid derivatives act on schizophrenia.

DISCLOSURE OF THE INVENTION

The present invention relates to a method for treating schizophrenia in a mammalian subject, which comprises administering to the subject in need thereof an effective amount of a fatty acid derivative represented by the formula (I):

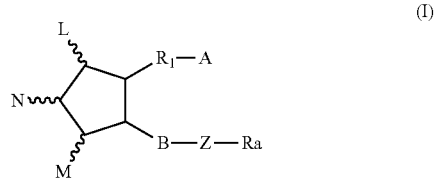

wherein L, M and N are hydrogen, hydroxy, halogen, lower alkyl, hydroxy(lower)alkyl, lower alkanoyloxy or oxo, wherein the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

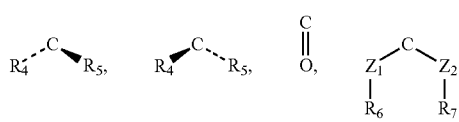

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time; Z$_1$ and Z$_2$ are oxygen, nitrogen or sulfur; R$_6$ and R$_7$ are optionally substituted lower alkyl, which is optionally linked together to form lower alkylene;

R$_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

The present invention also relates to a fatty acid derivative represented by the formula (I) as described above.

DETAILED DESCRIPTION OF THE INVENTION

The nomenclature of the fatty acid derivative used herein is based on the numbering system of the prostanoic acid represented in the above formula (A).

The formula (A) shows a basic skeleton of the C-20 fatty acid derivative, but the present invention is not limited to those having the same number of carbon atoms. In the formula (A), the numbering of the carbon atoms which constitute the basic skeleton of the fatty acid derivatives starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, the carbon atoms at the position 21 or later are named as a substituent at position 20. Stereochemistry of the compounds is the same as that of the above formula (A) unless otherwise specified.

In general, each of PGD, PGE and PGF represents a fatty acid derivative having hydroxy groups at positions 9 and/or 11, but in the present specification they also include those having substituents other than the hydroxy groups at positions 9 and/or 11. Such compounds are referred to as 9-deoxy-9-substituted-fatty acid derivatives or 11-deoxy-11-substituted-fatty acid derivatives. A fatty acid derivative having hydrogen in place of the hydroxy group is simply named as 9- or 11-deoxy-fatty acid derivative.

As stated above, the nomenclature of a fatty acid derivative is based on the prostanoic acid skeleton. In the case the compound has similar partial structure as the primary PG, the abbreviation of "PG" may be used. Thus, a fatty acid derivative whose α-chain is extended by two carbon atoms, that is, having 9 carbon atoms in the α-chain is named as 2-decarboxy-2-(2-carboxyethyl)-PG compound. Similarly, a fatty acid derivative having 11 carbon atoms in the α-chain is named as 2-decarboxy-2-(4-carboxybutyl)-PG compound. Further, a fatty acid derivative whose ω-chain is extended by two carbon atoms, that is, having 10 carbon atoms in the ω-chain is named as 20-ethyl-PG compound. These compounds, however, may also be named according to the IUPAC nomenclatures.

Examples of the analogues including substitution compounds or derivatives of the above described fatty acid derivative include a fatty acid derivative whose carboxy group at the end of the alpha chain is esterified; a fatty acid derivative whose α chain is extended, a physiologically acceptable salt thereof, a fatty acid derivative having a double bond between positions 2 and 3 or a triple bond between positions 5 and 6; a fatty acid derivative having substituent(s) on carbon atom(s) at position(s) 3, 5, 6, 16, 17, 18, 19 and/or 20; and a fatty acid derivative having a lower alkyl or a hydroxy (lower) alkyl group at position 9 and/or 11 in place of the hydroxy group.

According to the present invention, preferred substituents on the carbon atom at position(s) 3, 17, 18 and/or 19 include alkyl having 1-4 carbon atoms, especially methyl and ethyl. Preferred substituents on the carbon atom at position 16 include lower alkyls such as methyl and ethyl, hydroxy, halogen atom such as chlorine and fluorine, and aryloxy such as trifluoromethylphenoxy. Preferred substituents on the carbon atom at position 17 include lower alkyl such as methyl and ethyl, hydroxy, halogen atom such as chlorine and fluorine, and aryloxy such as trifluoromethylphenoxy. Preferred substituents on the carbon atom at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents on the carbon atom at position 5 include halogen atoms such as chlorine and fluorine. Preferred substituents on the carbon atom at position 6 include an oxo group forming a carbonyl group. Stereochemistry of PGs having hydroxy, lower alkyl or hydroxy (lower)alkyl substituent on the carbon atom at positions 9 and 11 may be α, β or a mixture thereof.

Further, the above described analogues or derivatives may have a ω chain shorter than that of the primary PGs and a substituent such as alkoxy, cycloalkyl, cycloalkyloxy, phenoxy and phenyl at the end of the truncated ω-chain.

A fatty acid derivative used in the present invention is represented by the formula (I):

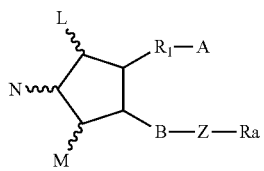

(I)

wherein L, M and N are hydrogen, hydroxy, halogen, lower alkyl, hydroxy(lower)alkyl, lower alkanoyloxy or oxo, wherein the five-membered ring may have at least one double bond;

A is —$CH_3$, or —$CH_2OH$, —$COCH_2OH$, —COOH or a functional derivative thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Z is

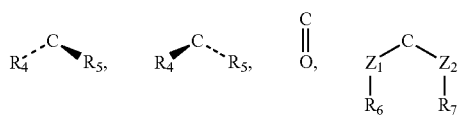

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time; $Z_1$ and $Z_2$ are oxygen, nitrogen or sulfur; $R_6$ and $R_7$ are optionally substituted lower alkyl, which is optionally linked together to form lower alkylene;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

A preferred compound used in the present invention is represented by the formula (II):

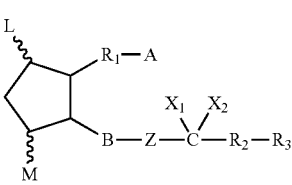

(II)

wherein L and M are hydrogen atom, hydroxy, halogen, lower alkyl, hydroxy(lower)alkyl, lower alkanoyloxy or oxo, wherein the five-membered ring may have one or more double bonds;

A is —$CH_3$, or —$CH_2OH$, —$COCH_2OH$, —COOH or a functional derivative thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$C≡C—;

Z is

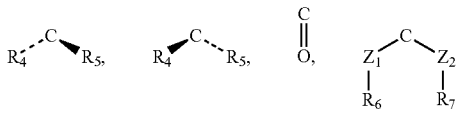

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time; $Z_1$ and $Z_2$ are oxygen, nitrogen or sulfur; $R_6$ and $R_7$ are optionally substituted lower alkyl, which is optionally linked together to form lower alkylene;

$X_1$ and $X_2$ are hydrogen, lower alkyl, or halogen;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

$R_2$ is a single bond or lower alkylene; and $R_3$ is lower alkyl, lower alkoxy, lower alkanoyloxy, cyclo(lower)alkyl, cyclo(lower)alkyloxy, aryl, aryloxy, heterocyclic group or heterocyclic-oxy group, and at least one of carbon atom in the aliphatic hydrocarbon is optionally substituted by oxygen, nitrogen or sulfur.

The present invention further relates to a novel compound of 7-[2-(4,4-difluoro-3-oxooctyl)-5-oxocyclopentyl]hept-2-enoic acid or a functional derivative thereof.

The compound may be present as a mixture of stereoisomers, or the compound may be present as a single stereoisomer.

In one embodiment, the present invention provides 7-[2-(4,4-difluoro-3-oxooctyl)-5-oxocyclopentyl]hept-2-enoic acid or an ether, an ester, an amide, tautomer, enantiomer or pharmaceutically acceptable salt thereof.

In another embodiment, the present invention provides (E)-7-[(1R,2R)-2-(4,4-difluoro-3-oxooctyl)-5-oxocyclopentyl]hept-2-enoic acid or an ether, an ester, an amide, tautomer or pharmaceutically acceptable salt thereof.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions. The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or arylsulfonylamides such as methylsulfonylamide, ethylsulfonylamide and tolylsulfonylamide.

Preferred examples of L and M include hydrogen, hydroxy and oxo, and especially, L and M are both hydroxy, or L is oxo and M is hydrogen or hydroxy.

Preferred example of A is —COOH, its pharmaceutically acceptable salt, ester or amide thereof.

Preferred example of $X_1$ and $X_2$ are both being hydrogen or halogen atoms, more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:

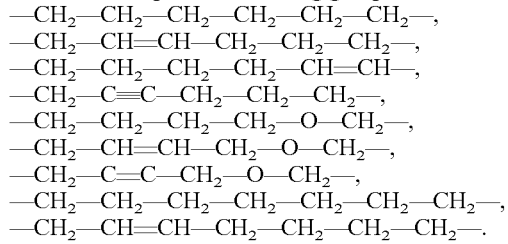

—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred Ra is a hydrocarbon containing 1-10 carbon atoms, more preferably, 1-8 carbon atoms. Ra may have one or two side chains having one carbon atom. Further, at least one carbon atom in the aliphatic hydrocarbon is optionally substituted by oxygen, nitrogen or sulfur.

In embodiments of the present invention, representative compounds of the formula (I) or (II) include compounds of the formula (I) wherein Ra is substituted by halogen and/or Z is C=O;
compounds of the formula (II) wherein one of $X_1$ and $X_2$ is substituted by halogen and/or Z is C=O;
compounds of the formula (II) wherein L is =O or —OH, M is H or OH, A is COOH or a functional derivative thereof, B is —$CH_2$—$CH_2$—, Z is C=O, $X_1$ is halogen (e.g. $X_1$ is Cl, Br, I or F) or hydrogen, $X_2$ is halogen (e.g. $X_2$ is Cl, Br, I or F) or hydrogen, $R_1$ is a saturated or unsaturated bivalent straight $C_6$ aliphatic hydrocarbon residue, $R_2$ is a single bond, and $R_3$ is straight or branched lower alkyl (e.g. $C_{4-6}$ alkyl) optionally substituted by oxygen, nitrogen or sulfur;
compounds of the formula (II) wherein L is =O, M is OH, A is COOH or a functional derivative thereof, B is —$CH_2$—$CH_2$—, Z is C=O, $X_1$ is halogen (e.g. $X_1$ is Cl, Br, I or F) or hydrogen, $X_2$ is halogen (e.g. $X_2$ is Cl, Br, I or F) or hydrogen, $R_1$ is a saturated or unsaturated bivalent straight $C_6$ aliphatic hydrocarbon residue, $R_2$ is a single bond, and $R_3$ is straight or branched lower alkyl optionally substituted by oxygen, nitrogen or sulfur;
compounds of the formula (II) wherein L is =O, M is OH, A is COOH or a functional derivative thereof, B is —$CH_2$—$CH_2$—, Z is C=O, $X_1$ and $X_2$ are halogen atoms (e.g. $X_1$ and $X_2$ are Cl, Br, I or F), $R_1$ is a saturated or unsaturated bivalent straight $C_6$ aliphatic hydrocarbon residue, $R_2$ is a single bond, and $R_3$ is straight or branched lower alkyl (e.g. $C_4$ alkyl or $C_5$ alkyl);
compounds of the formula (II) wherein L is =O, M is OH, A is COOH or a functional derivative thereof, B is —$CH_2$—$CH_2$—, Z is C=O, $X_1$ and $X_2$ are fluorine atoms, $R_1$ is a saturated or unsaturated bivalent straight $C_6$ aliphatic hydrocarbon residue, $R_2$ is a single bond, and $R_3$ is straight or branched lower alkyl (e.g. $C_4$ alkyl or $C_5$ alkyl);
compounds of the formula (II) wherein L is =O, M is H or OH, A is COOH or a functional derivative thereof, B is —$CH_2$—$CH_2$—, Z is C=O, $X_1$ and $X_2$ are halogen atoms (e.g. $X_1$ and $X_2$ are Cl, Br, I or F), $R_1$ is a saturated or unsaturated bivalent straight $C_6$ aliphatic hydrocarbon residue, $R_2$ is a single bond, and $R_3$ is —$CH_2$—$CH_2$—$CH_2$—$CH_3$ or —$CH_2$—CH($CH_3$)—$CH_2$—$CH_3$;
7-[2-(4,4-difluoro-3-oxooctyl)-5-oxocyclopentyl]heptanoic acid;
isopropyl-7-[3,5-dihydroxy-2-(3-oxodecyl)cyclopentyl]hept-5-enoate;
7-[2-(4,4-difluoro-3-oxooctyl)-5-oxocyclopentyl]hept-2-enoic acid; and
an ether, an ester, an amide, tautomer, enantiomer or pharmaceutically acceptable salt thereof.

In further embodiment, representative compounds used in the present invention include (−)-7-[(2R,4aR,5R,7aR)-2-(1,1-difluoropentyl)-2-hydroxy-6-oxooctahydrocyclopenta[b]pyran-5-yl]heptanoic acid (lubiprostone), (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid (cobiprostone), (+)-isopropyl (Z)-7-[(1R,2R,3R,5S)-3,5-dihydroxy-2-(3-oxodecyl)cyclopentyl]hept-5-enoate (isopropyl unoprostone) (−)-7-[(1R,2R)-2-(4,4-difluoro-3-oxooctyl)-5-oxocyclopentyl]heptanoic acid, (E)-7-[(1R,2R)-2-(4,4-difluoro-3-oxooctyl)-5-oxocyclopentyl]hept-2-enoic acid, a tautomeric isomer thereof and a functional derivative thereof.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the fatty acid derivative which is dihydro between 13 and 14, and keto(=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the fatty acid derivatives used in the invention include the bicyclic compound and analogs or derivatives thereof.

The bicyclic compound is represented by the formula (III)

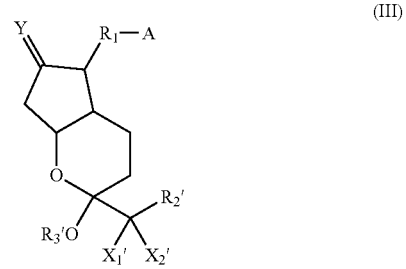

(III)

wherein, A is —$CH_3$, or —$CH_2OH$, —$COCH_2OH$, —COOH or a functional derivative thereof;
$X_1'$ and $X_2'$ are hydrogen, lower alkyl, or halogen;
Y is

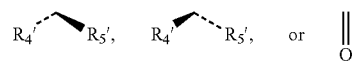

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.
$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group, and at least one of carbon atom in the aliphatic hydrocarbon is optionally substituted by oxygen, nitrogen or sulfur.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073, 569, 5,166,174, 5,221,763, 5,212,324, 5,739,161 and 6,242, 485 (these cited references are herein incorporated by reference).

The mammalian subject may be any mammalian subject including a human. The compound may be applied systemically or topically. Usually, the compound may be administered by oral administration, intranasal administration, inhalational administration, intravenous injection (including infusion), subcutaneous injection, intra rectal administration, intra vaginal administration, transdermal administration and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.00001-500 mg/kg per day, more preferably 0.0001-100 mg/kg.

The compound may preferably be formulated in a pharmaceutical composition suitable for administration in a conventional manner. The composition may be those suitable for oral administration, intranasal administration, inhalational administration, injection or perfusion as well as it may be an external agent, suppository or pessary.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Example of the intranasal preparations may be aqueous or oily solutions, suspensions or emulsions comprising one or more active ingredient. For the administration of an active ingredient by inhalation, the composition of the present invention may be in the form of suspension, solution or emulsion which can provide aerosol or in the form of powder suitable for dry powder inhalation. The composition for inhalational administration may further comprise a conventionally used propellant.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The present external agent includes all the external preparations used in the fields of dermatology and otolaryngology, which includes ointment, cream, lotion and spray.

Another form of the present invention is suppository or pessary, which may be prepared by mixing active ingredients into a conventional base such as cacao butter that softens at body temperature, and nonionic surfactants having suitable softening temperatures may be used to improve absorbability.

According to the present invention, the fatty acid derivatives of the present invention are useful for treating schizophrenia.

The term "treating" or "treatment" used herein includes prophylactic and therapeutic treatment, and any means of control such as prevention, care, relief of the condition, attenuation of the condition, arrest of progression, etc.

The pharmaceutical composition of the present invention may contain a single active ingredient or a combination of two or more active ingredients, as far as they are not contrary to the objects of the present invention.

In a combination of plural active ingredients, their respective contents may be suitably increased or decreased in consideration of their therapeutic effects and safety.

The term "combination" used herein means two or more active ingredient are administered to a patient simultaneously in the form of a single entity or dosage, or are both administered to a patient as separate entities either simultaneously or sequentially with no specific time limits, wherein such administration provides therapeutically effective levels of the two components in the body, preferably at the same time.

In one embodiment, the fatty acid derivatives of the present invention inhibit reduction of prepulse inhibition which is a measure of sensorimotor gating, a pre-conscious regulator of attention.

The present invention will be described in detail with reference to the following example, which, however, is not intended to limit the scope of the present invention.

Example 1

Effects of Compound A and B on Schizophrenia Model (PCP-Disrupted PPI Response in Rats)

Method

Male Wistar rats (n=135) (200-300 g) were used. Animals are housed at a standard temperature (22±1° C.) and in a light-controlled environment (lights on from 7 am to 8 pm) with ad libitum access to food and water. Animals are treated with Phencyclidine (PCP) at 1.5 mg/kg, s.c., and tested in Pre-Pulse Inhibition (PPI) 15 min later. Intravenous administration of Compound A ((−)-7-[(1R,2R)-2-(4,4-difluoro-3-oxooctyl)-5-oxocyclopentyl]heptanoic acid), Compound B ((+)-isopropyl (Z)-7-[(1R,2R,3R,5S)-3,5-dihydroxy-2-(3-oxodecyl)cyclopentyl]hept-5-enoate) and corresponding vehicle was done 15 min before PPI, which means each compound or vehicle was administered immediately before PCP injection.

PPI tests were conducted in standard startle chambers (SR-LAB Startle Response system, San Diego Instruments, USA). Before the PPI testing, the animals were habituated to handling. On the day of PPI testing, the animals were placed in the chamber and allowed to habituate for a period of 300 s. After habituation period, the rats received 12 startle trials, 12 no-stimulus trials, and 12 trials of the pre-pulse/startle trials (3×12 trials). The startle trials consists of single 110 dB white noise burst lasting 20 ms. The PPI trials consist of a pre-pulse (20 ms burst of white noise with intensities of 60 dB) followed 100 ms later by a startle stimulus (110 dB, 20 ms white noise). During the no-stimulus trial, no startle noise is presented. The resulting movement of the rat in the startle chamber is measured during 100 ms after startle stimulus onset. Basal startle amplitude is determined as the mean amplitude of the 12 startle trials. % PPI is calculated according to the formula $100-100\% \times (PP/P110)$, in which PP is the mean of the 12 pre-pulse inhibition trials (i.e., for each individual pre-pulse intensity), and P110 is the basal startle amplitude. The animals are treated with PCP s.c. and then tested in PPI 15 min later.

Results

Compound A and B improved the PCP-disrupted PPI response.

TABLE 1

| Compound | Dose (mg/kg) | PCP-treatment | % PPI (Mean ± SEM) |
|---|---|---|---|
| Vehicle | 0 | — | 42.2 ± 4.3 |
| Vehicle | 0 | X | 19.8 ± 5.6 |
| Compound A | 0.5 | X | 34.2 ± 3.9 |
| Compound B | 0.5 | X | 40.5 ± 4.2 |

The above result indicates that the present compounds are useful for the treatment of schizophrenia.

Example 2

Effects of Compound B and C on PCP-Disrupted PPI Response in Rats

Method

Male Wistar rats (n=135) (200-300 g) were used. Animals are housed at a standard temperature (22±1° C.) and in a light-controlled environment (lights on from 7 am to 8 pm) with ad libitum access to food and water. Animals are treated with Phencyclidine (PCP) at 1.5 mg/kg, s.c., and tested in Pre-Pulse Inhibition (PPI) 15 min later. Oral administration of Compound B ((+)-isopropyl (Z)-7-[(1R,2R,3R,5S)-3,5-dihydroxy-2-(3-oxodecyl)cyclopentyl]hept-5-enoate) and Compound C ((E)-7-[(1R,2R)-2-(4,4-difluoro-3-oxooctyl)-5-oxocyclopentyl]hept-2-enoic acid) and corresponding vehicle was done 45 min before PPI, which means each compound or vehicle was administered 30 min before PCP injection.

PPI tests were conducted in standard startle chambers (SR-LAB Startle Response system, San Diego Instruments, USA). Before the PPI testing, the animals were habituated to handling. On the day of PPI testing, the animals were placed in the chamber and allowed to habituate for a period of 300 s. After habituation period, the rats received 12 startle trials, 12 no-stimulus trials, and 12 trials of the pre-pulse/startle trials (3×12 trials). The startle trials consists of single 110 dB white noise burst lasting 20 ms. The PPI trials consist of a pre-pulse (20 ms burst of white noise with intensities of 63 dB) followed 100 ms later by a startle stimulus (110 dB, 20 ms white noise). During the no-stimulus trial, no startle noise is presented. The resulting movement of the rat in the startle chamber is measured during 100 ms after startle stimulus onset. Basal startle amplitude is determined as the mean amplitude of the 12 startle trials. % PPI is calculated according to the formula $100-100\% \times (PP/P110)$, in which PP is the mean of the 12 pre-pulse inhibition trials (i.e., for each individual pre-pulse intensity), and P110 is the basal startle amplitude. The animals are treated with PCP s.c. and then tested in PPI 15 min later.

Results

Compound B and C improved the PCP-disrupted PPI response.

TABLE 2

| Compound | Dose (mg/kg) | PCP-treatment | % PPI (Mean ± SEM) |
|---|---|---|---|
| Vehicle | 0 | — | 46.7 ± 5.2 |
| Vehicle | 0 | X | 6.8 ± 6.5 |
| Compound B | 0.3 | X | 24.0 ± 5.3 |
| Compound C | 0.3 | X | 24.7 ± 5.0 |

Synthesis Example of (E)-7-[(1R,2R)-2-(4,4-difluoro-3-oxooctyl)-5-oxocyclopentyl]hept-2-enoic Acid
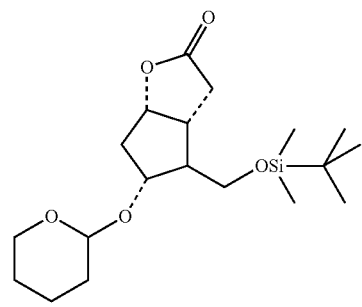
NS-C4
[1]
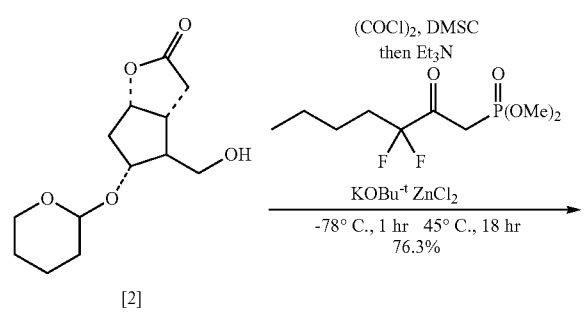
[2]
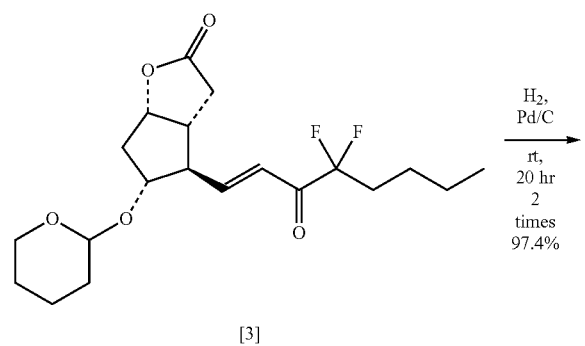
[3]
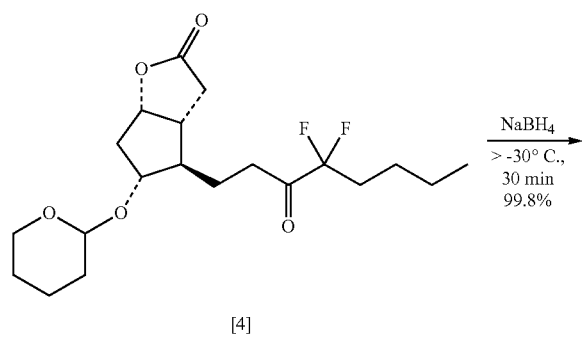
[4]
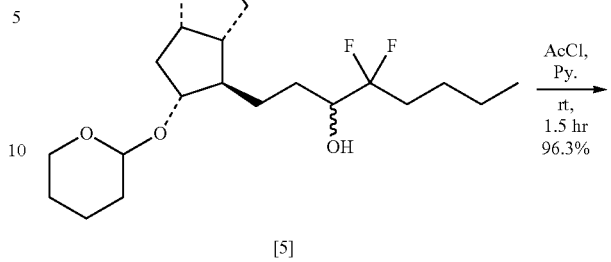
[5]
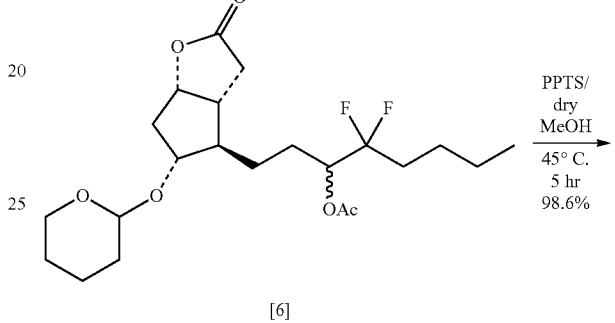
[6]
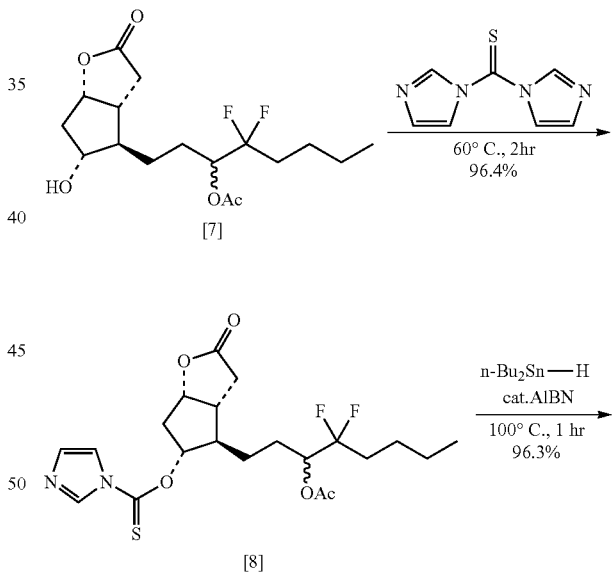
[7]
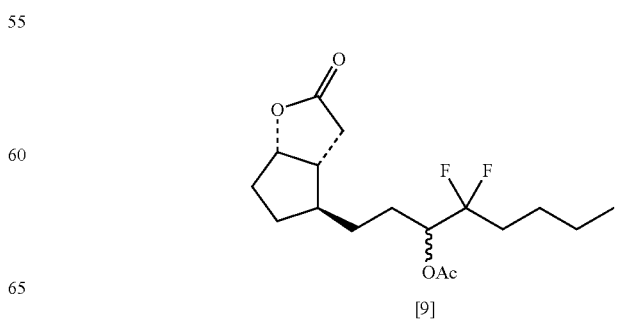
[8]
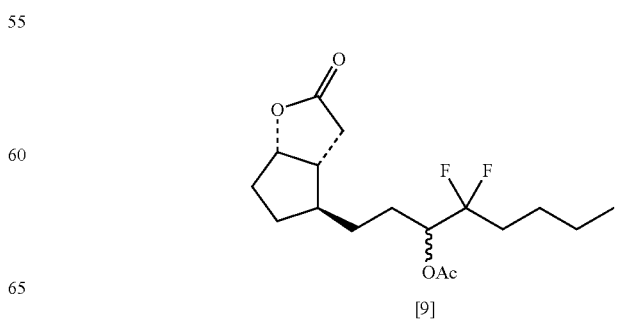
[9]

17
-continued

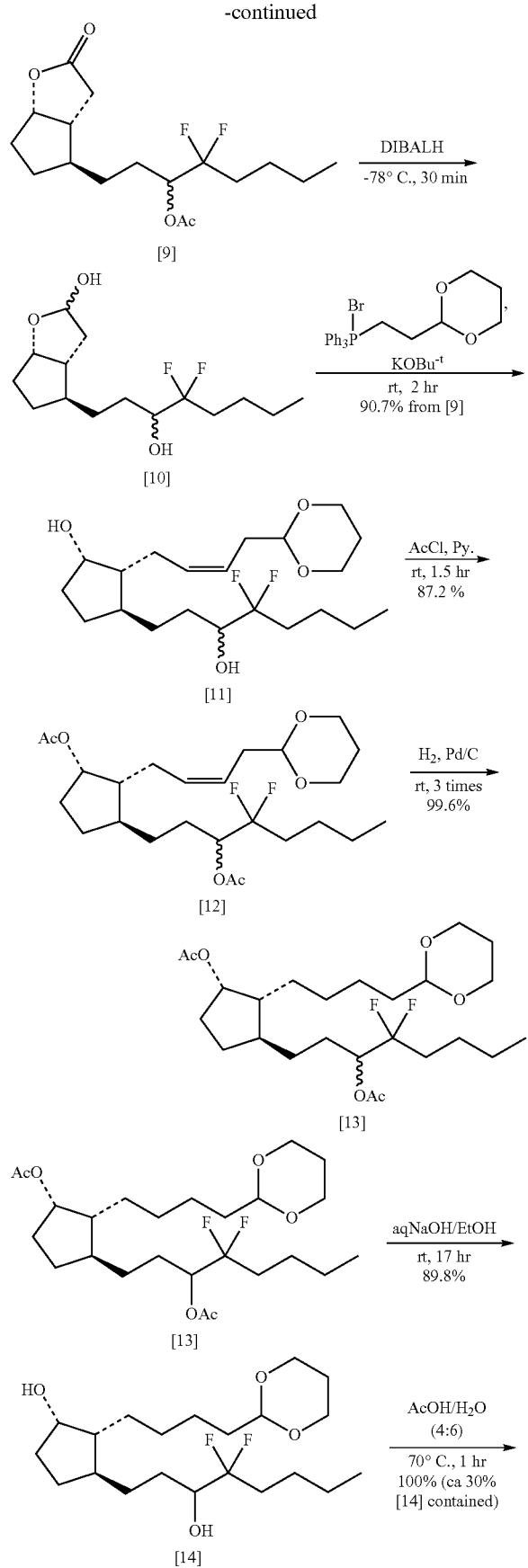

18
-continued

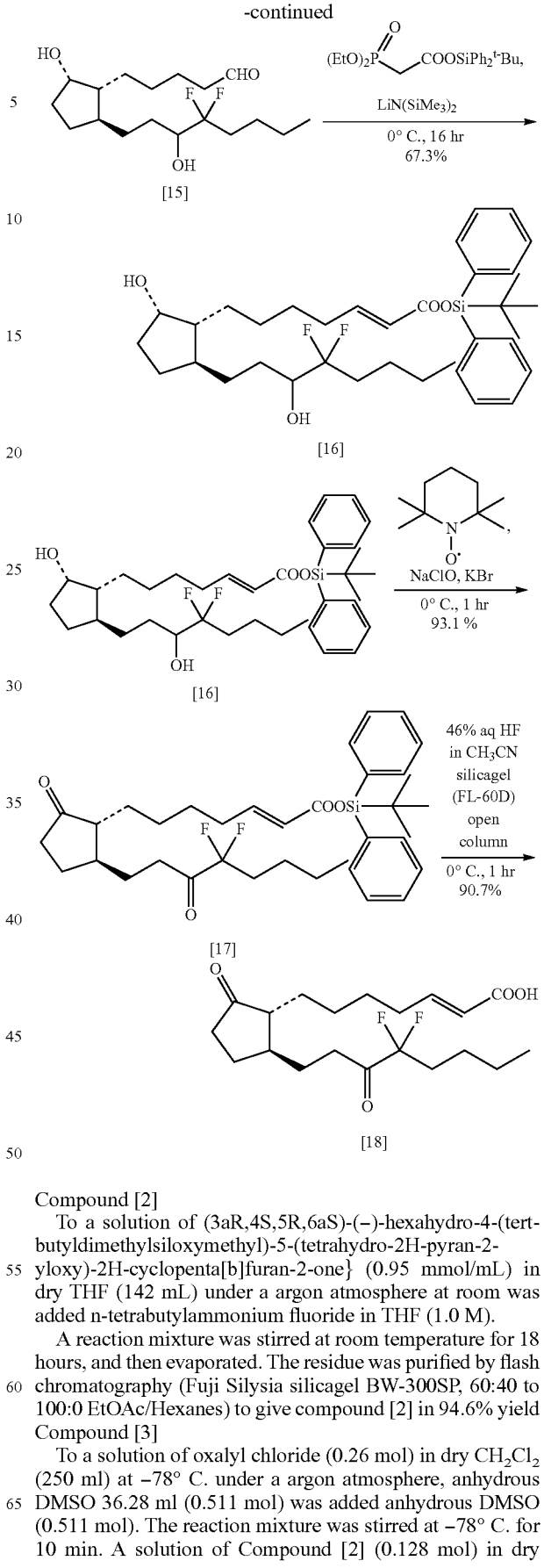

Compound [2]

To a solution of (3aR,4S,5R,6aS)-(−)-hexahydro-4-(tert-butyldimethylsiloxymethyl)-5-(tetrahydro-2H-pyran-2-yloxy)-2H-cyclopenta[b]furan-2-one} (0.95 mmol/mL) in dry THF (142 mL) under a argon atmosphere at room was added n-tetrabutylammonium fluoride in THF (1.0 M).

A reaction mixture was stirred at room temperature for 18 hours, and then evaporated. The residue was purified by flash chromatography (Fuji Silysia silicagel BW-300SP, 60:40 to 100:0 EtOAc/Hexanes) to give compound [2] in 94.6% yield Compound [3]

To a solution of oxalyl chloride (0.26 mol) in dry $CH_2Cl_2$ (250 ml) at −78° C. under a argon atmosphere, anhydrous DMSO 36.28 ml (0.511 mol) was added anhydrous DMSO (0.511 mol). The reaction mixture was stirred at −78° C. for 10 min. A solution of Compound [2] (0.128 mol) in dry CH$_2$Cl$_2$ (100 mL) was added to the mixture and stirred at −78° C. for 1 h followed by addition of dry triethylamine (89 ml). The reaction mixture was warmed to room temperature, poured into aqNH$_4$Cl (500 ml) and extracted with CH$_2$C$_2$. The organic layer was then washed with aqNH$_4$Cl and brine, dried over MgSO$_4$, filtered and concentrated. The crude aldehyde was used for the next step without further purification.

To a solution of 3,3-difluoro-2-oxo-hexyl-dimethylphosphonate (0.192 mol) dry THF (100 ml) at 0° C. under argon atmosphere was added potassium tert-butoxide (1.0M in THF). The reaction mixture was stirred and warmed to room temperature for 30 min anhydrous zinc chloride (0.192 mol) was added to the reaction mixture and stirred at room temperature for 3 h. The reactions were then mixed with a solution of the aldehyde above in dry THF (100 ml), and were stirred at 45° C. for 18 h. The mixture was poured into aqNH$_4$Cl (400 ml) and extracted with ethyl acetate three times. The combined organic layer was washed with 1N—HCl, aqNaHCO$_3$ and brine then dried over MgSO$_4$, filtered and concentrated. The crude residue was purified by flash chromatography (Fuji Silysia silicagel BW-300SP, 30:70 to 60:40 EtOAc/Hexanes) to give compound [3] in 76.3% yield.

$^1$H-NMR (400 MHz, CDCl$_3$) δ 6.98 (1H, m,), 6.60 (1H, m,), 5.03 (1H, m,), 4.65 (1H, m,), 4.25-4.05 (1H, m,), 3.78 (1H, m,), 3.50 (1H, m,), 2.92-1.35 (18H, m,), 0.92 (3H, t, J=7.2 Hz,)

Compound [4]

To a solution of compound [3] (0.0959 mol) in ethyl acetate was added 5% Pd/C 3.70 g (10 wt %). The mixture was stirred for 20 h at room temperature under H$_2$ atmosphere. The reaction mixture was filtrated, washed with ethyl acetate and concentrated to give.

The same reaction was repeated 2 times, the filtrate was concentrated and give compound [4] in 97.4% yield Compound [5]

To a solution of compound [4] (0.0934 mol) in dry methanol was added solid NaBH$_4$ (0.0467 mol) at −40° C. under argon atmosphere. The reaction mixture was stirred at −30° C./−40° C. for 30 min. Acetic acid (5.6 ml) was added to the reaction, poured into H$_2$O and extracted with ethyl acetate three times. The combined organic layer was then washed with aqNaHCO$_3$ and brine, dried over MgSO$_4$, filtered, and concentrated to give compound [5] in 99.8% yield.

Compound [6]

To a solution of alcohol [5] (0.0932 mol) in dry CH$_2$Cl$_2$ (255 ml) was added dropwise anhydrous pyridine (0.373 mol) and acetyl chloride (0.186 mol) under argon atmosphere at 0° C. The reaction mixture was stirred for 1.5 h at room temperature, and poured into H$_2$O. The mixture was extracted with CH$_2$Cl$_2$. The organic layer was washed with 1N—HCl, aqNaHCO$_3$ and brine, dried over MgSO$_4$, filtered, and concentrated. The crude residue was purified by flash chromatography (Fuji Silysia silicagel BW-300SP, 30:70 to 45:65 EtOAc/Hexanes) to give compound [6] in 96.3% yield.

$^1$H-NMR (400 MHz, CDCl$_3$) δ 5.09 (2H, m,), 4.66 (1H, m,), 4.10-3.78 (2H, m,), 3.51 (1H, m,), 2.81 (1H, m,), 2.65-1.20 (24H, m,), 0.90 (3H, t, J=7.2 Hz,)

Compound [7]

To a solution of compound [6] (88.8 mmol) in dry methanol (307 ml) was added solid pyridinium p-toluenesulfonate (PPTS (8.88 mmol) under argon atmosphere at room temperature. The reaction mixture was stirred for 5 h at 45° C. The mixture was poured into brine and extracted with ethyl acetate. The organic layer was washed with aqNaHCO$_3$ and brine then dried over MgSO$_4$, filtered, and concentrated. The crude residue was purified by flash chromatography (Fuji Silysia silicagel BW-300SP) of the crude residue using hexane and ethyl acetate (50:50 to 70:30 EtOAc/Hexanes) to give compound [7] in 98.6% yield.

Compound [8]

To a stirred solution of compound [7] (88.4 mmol) in dry dichloroethane (246 ml) was added solid thiocarbonyldiimidazole (0.133 mol) under argon atmosphere at room temperature. The reaction mixture was stirred for 2 h at 60° C. The mixture was concentrated. The crude residue was purified by flash chromatography (Fuji Silysia silicagel BW-300SP, 60:40 to 70:30 EtOAc/Hexanes) to give compound [8] in 98.4% yield.

$^1$H-NMR (400 MHz, CDCl$_3$) δ 8.36 (1H, s,), 7.56 (1H, m,), 7.04 (1H, s,), 5.69 (1H, m,), 5.10 (2H, m,), 2.96 (1H, dd, J=18.4, 10.4 Hz), 2.72 (1H, m,), 2.52 (3H, m,), 2.25 (1H, m,), 2.15-2.13 (3H, m,), 1.95-1.30 (10H, m,), 0.92 (3H, t, J=7.2 Hz,)

Compound [9]

To a mixture of tributyltin hydride (0.113 mol) and AIBN (azobisisobutyronitrile) (4.35 mmol) in dry toluene (200 ml) was added a solution of compound [8] (87.0 mmol) in dry toluene (300 ml) under argon atmosphere at 100° C., and the reaction was stirred for 30 min at 100° C. Tributyltin hydride 15.0 ml (0.0558 mol) was added to the reaction mixture solution, and was stirred further for 30 min at 100° C.

The mixture was concentrated and diluted with hexane (350 ml) and extracted with acetonitrile. The acetonitrile layer was concentrated and crude residue was purified by flash chromatography (Fuji Silysia silicagel BW-300SP 30:70 to 40:60 EtOAc/Hexanes) to give compound [9] in 96.3% yield.

$^1$H-NMR (400 MHz, CDCl$_3$) δ 5.11 (1H, m,), 4.94 (1H, m,), 2.79 (1H, m,), 2.36 (2H, m,), 2.15 (3H, s,), 2.17-1.16 (15H, m,), 0.92 (3H, t, J=7.2 Hz,)

Compound [11]

To a stirred solution of compound [9] (0.0837 mol) in dry toluene (195 ml) was added diisobutylaluminum hydride (DIBAL, 1.5M in toluene) (0.293 mol) at −78° C. under argon atmosphere. The reaction mixture was stirred at −78° C. for 30 min. Methanol (195 ml) was added to the mixture and warmed to room temperature. Then aq potassium sodium tartrate (500 ml) was added to the reaction and stirred at room temperature for 1 h. The mixture was extracted with ethyl ether. The organic layer was washed with brine, dried over MgSO$_4$, filtered, and concentrated to give crude compound [10].

To a suspension of 2-(1,3-dioxane-2-yl)-ethyltriphenylphosphonium bromide (0.243 mol) in dry THF (450 ml) was added solid potassium t-butoxide (0.243 mol) at 0° C. under argon atmosphere. The suspension was stirred at room temperature for 40 min.

A solution of compound [10] in dry THF (80 ml) was added to the suspension, and stirred at room temperature for 2 h. The mixture poured into ice/H$_2$O and extracted with ethyl acetate. The organic layer was washed with H$_2$O and brine then dried over MgSO$_4$, filtered, and concentrated. The crude residue was purified by flash chromatography (Fuji Silysia silicagel BW-300SP 40:60 to 60:40 EtOAc/Hexanes) to give compound [11] in 90.7% yield from compound [9].

Compound [12]

To a solution of compound [11] (0.0759 mol) in dry CH$_2$Cl$_2$ (350 ml) was added dropwise anhydrous pyridine (0.607 mol) and acetyl chloride (0.304 mol) under argon atmosphere at 0° C. The reaction mixture was stirred for 1.5 h at room temperature, and poured into H$_2$O. The mixture was extracted with CH$_2$Cl$_2$. The organic layer was washed with 1N—HCl, aqNaHCO$_3$ and brine then dried over MgSO$_4$, filtered, and concentrated. The crude residue was purified by flash chromatography (Fuji Silysia silicagel BW-300SP, 20:800 to 30:70) to give compound [12] in 87.2% yield.

$^1$H-NMR (400 MHz, CDCl$_3$) δ 5.43 (2H, m,), 5.10 (2H, m,), 4.50 (1H, t, J=5.6 Hz) 4.09 (2H, m,), 3.75 (2H, m,), 2.40-1.05 (28H, m,), 0.92 (3H, t, J=7.2 Hz,)

Compound [13]

To a solution of compound [12] (0.0661 mol) in ethyl acetate (310 ml) was added 5% Pd/C 3.14 g (10 wt %). The reaction mixture was stirred for 16 h at room temperature under H$_2$ atmosphere.

The mixture was filtrated with Celite-pad and washed with ethyl acetate.

the organic layer was filtrate was concentrated to give compound [13] in 99.6% yield.

Compound [14]

to a solution of compound [13] (0.0658 mol) in ethanol (165 ml) was added 2N-aq NaOH (0.329 mol) at 0° C. The reaction mixture was stirred for 17 h at room temperature. The mixture was neutralized with 2N-aq HCl and extracted with ethyl acetate. The organic layer was washed with H$_2$O and brine then dried over MgSO$_4$, filtered, and concentrated. The crude residue was purified by flash chromatography (Fuji Silysia silicagel BW-300SP, 50:50/60:40) to give compound [14] in 89.6% yield.

$^1$H-NMR (400 MHz, CDCl$_3$) δ 4.52 (1H, t, J=5.6 Hz) 4.22 (1H, bs,), 4.10 (2H, m,) 3.76 (2H, m,), 3.71 (1H, m,), 2.18-1.09 (26H, m,), 0.93 (3H, t, J=7.2 Hz,)

Compound [16]

To a stirred solution of compound [14] (0.0590 mol) in glacial acetic acid (232 ml) was added distilled water for 15 min at 70° C. The reaction mixture was stirred for 45 min at 70° C. The mixture was concentrated. The crude residue was purified by flash chromatography (Fuji Silysia silicagel BW-300SP, 50:50 to 60:40 EtOAc/Hexanes) to give compound [15].

To a solution of tert-butyldiphenylsilyl diethylphosphonoacetate (0.0767 mol) in dry THF (77 ml) was added lithium bis(trimethylsilyl)amide (1.0M in THF) (0.0767 mol) at 0° C. under argon atmosphere. The reaction mixture was stirred at room temperature for 1 h. a solution of compound [15] 22.50 g in dry THF (70 ml) was added At −40° C. and then the reaction mixture was stirred at 0° C. for 17 h. The mixture was acidified with acetic acid (0.153 mol) and poured into H$_2$O. The mixture was extracted with ethyl acetate. The organic layer was washed with H$_2$O, agNaHCO$_3$ and brine then dried over MgSO$_4$, filtered, and concentrated. The crude residue was purified by flash chromatography (Fuji Silysia silicagel BW-300SP, 30:70 to 35:65) to give compound [16] in 67.3% yield from compound [14].

$^1$H-NMR (400 MHz, CDCl$_3$) δ 7.70-7.36 (10H, m,), 7.07 (1H, dt, J=15.6, 6.8 Hz), 5.93 (1H, d, J=15.6 Hz), 4.22 (1H, bs,), 3.66 (1H, m,), 2.25 (2H, m,), 2.05-1.02 (31H, m,), 0.93 (3H, t, J=7.2 Hz,)

Compound [17]

To a solution of compound [16] (0.0625 mol) in toluene (577 ml) was added potassium bromide (0.125 mol), 2,2,6,6-tetramethylpiperidine 1-oxyl (TEMPO, 0.0125 mol), and 3%-aq NaHCO$_3$ (0.125 mol) and then cooled to 0° C. After addition of ca 0.9M-aq sodium hypochlorite, the mixture was stirred at 0° C. for 45 min. aq Sodium thiosulfate (400 ml) was added and extracted with ethyl ether. The organic layer was washed with 1N—HCl (200 ml), agNaHCO$_3$ (400 ml) and brine (400 ml), then dried over MgSO$_4$, filtered and concentrated. The crude residue was purified by flash chromatography (Fuji Silysia silicagel BW-300SP, 10:90 to 20:80) to give compound [17] in 93.1% Yield.

Compound [18]

(E)-7-[(1R,2R)-2-(4,4-difluoro-3-oxooctyl)-5-oxocyclopentyl]hept-2-enoic acid (7-[(1R,2R)-2-(4,4-difluoro-3-oxo-octyl)-5-oxo-cyclopentyl]-hept-2(E)-enoic acid)

To a solution of compound [17] (0.0582 mol) in acetonitrile (356 ml) was added 46%-aq hydrogen fluoride (0.582 mol) at 0° C. The reaction mixture was stirred at 0° C. for 1 h. The mixture was added with Water (300 ml) and brine (200 ml) were added to the reaction and extracted with ethyl ether. The organic layer was washed with water and brine, then dried over MgSO$_4$, filtered, and concentrated. The crude residue was purified by flash chromatography (Fuji Silysia silicagel FL-60D, 0:100, 10:90, 20:80, 30:70 to 35:65 EtOAc/Hexanes) to give Compound [18] in 90.7% yield.

$^1$H-NMR (400 MHz, CDCl$_3$) δ 7.06 (1H, dt, J=15.6, 7.2 Hz,), 5.83 (1H, d, J=15.6 Hz,), 2.76 (2H, m,), 2.40-1.20 (22H, m,), 0.93 (3H, t, J=6.8 Hz,)

$^{13}$C-NMR (100 MHz, CDCl$_3$) δ 220.1, 201.0 (t, J=32 Hz), 171.58, 151.95, 120.71, 118.39 (t, J=251 Hz), 54.84, 40.69, 37.72, 33.85, 32.18 (t, J=22 Hz), 32.12, 28.13, 27.53, 27.32, 26.75, 26.31, 23.31 (t, J=5 Hz), 22.41, 13.76

IR (neat) 2959, 2934, 1740, 1697, 1649, 1285, 1213, 1165, 1028, 984, 914 cm$^{-1}$

What is claimed is:

1. A method for treating schizophrenia in a mammalian subject, which comprises administering to the subject in need thereof an effective amount of a compound selected from the group consisting of (−)-7-[(1R,2R)-2-(4,4-difluoro-3-oxooctyl)-5-oxocyclopentyl]heptanoic acid, (+)-isopropyl (Z)-7-[(1R,2R,3R,5S)-3,5-dihydroxy-2-(3-oxodecyl)cyclopentyl] hept-5-enoate and (E)-7-[(1R,2R)-2-(4,4-difluoro-3-oxooctyl)-5-oxocyclopentyl]hept-2-enoic acid.

2. The method as described in claim 1, wherein the compound is (−)-7-[(1R,2R)-2-(4,4-difluoro-3-oxooctyl)-5-oxocyclopentyl]heptanoic acid.

3. The method as described in claim 1, wherein the compound is (+)-isopropyl (Z)-7-[(1R,2R,3R,5S)-3,5-dihydroxy-2-(3-oxodecyl)cyclopentyl]hept-5-enoate.

4. The method as described in claim 1, wherein the compound is (E)-7-[(1R,2R)-2-(4,4-difluoro-3-oxooctyl)-5-oxocyclopentyl]hept-2-enoic acid.

* * * * *